United States Patent [19]

Dahms

[11] Patent Number: 5,246,863
[45] Date of Patent: Sep. 21, 1993

[54] KARL FISCHER TITRATION TECHNIQUES

[76] Inventor: Harald Dahms, 472 Madison Ave., Toms River, N.J. 08753

[21] Appl. No.: 808,062

[22] Filed: Dec. 9, 1991

Related U.S. Application Data

[63] Continuation of Ser. No. 723,694, Jun. 24, 1991, abandoned, which is a continuation of Ser. No. 237,539, Aug. 29, 1988, abandoned.

[51] Int. Cl.$^5$ .......................................... G01N 33/18
[52] U.S. Cl. ...................................... 436/42; 435/51; 435/163; 435/180; 422/75; 204/153.22; 204/153.23
[58] Field of Search ............... 436/42, 51, 163, 150, 436/180; 204/153.22, 153.23, 405; 422/75

[56] References Cited

U.S. PATENT DOCUMENTS

| | | | |
|---|---|---|---|
| 3,826,971 | 7/1974 | Jasinohi et al. | 204/153.23 |
| 3,870,466 | 3/1975 | Rellstab et al. | 436/51 |
| 4,005,983 | 2/1977 | Dahms | 436/42 |
| 4,120,657 | 10/1978 | Nagy et al. | 422/75 |
| 4,211,614 | 7/1980 | Eppstein et al. | 436/42 |
| 4,664,756 | 5/1987 | Shimizu et al. | 436/42 |
| 4,749,552 | 6/1988 | Sakisako et al. | 422/75 |
| 4,859,608 | 8/1989 | Frueh | 422/75 |
| 4,865,992 | 9/1989 | Hach et al. | 422/75 |

FOREIGN PATENT DOCUMENTS 57-23856 2/1982 Japan ..................................... 422/75

Primary Examiner—W. Gary Jones
Assistant Examiner—Todd J. Burns

[57] ABSTRACT

An improved technique and apparatus for automatic titration for determining the water content of a sample by a Karl Fischer (K.F.) reaction. Rather than requiring titration from one endpoint to another identical endpoint, each determination is made using a calibration relative to the water equivalent of a known amount of titrant together with the change in sensor output that occurs when a sample is added to the K.F. reagent. Improved accuracy and speed of analysis results.

49 Claims, 3 Drawing Sheets

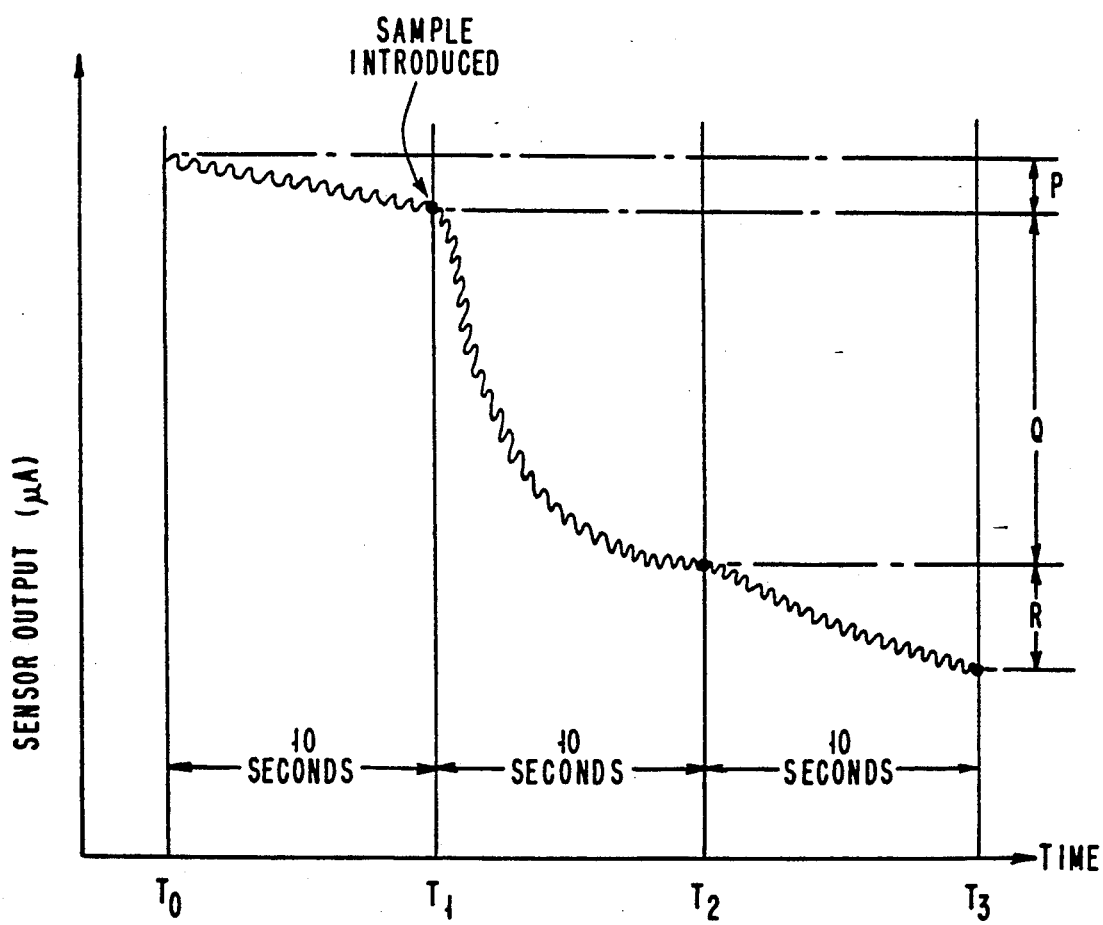

KARL FISCHER TITRATION TECHNIQUES

This is a continuation of copending application Ser. No. 07/723,694 filed Jun. 24, 1991, now abandoned which is a continuation of 07/237,539 filed on Aug. 29, 1988, now abandoned.

BACKGROUND

1. Field of the Invention

This invention relates to techniques having increased speed and accuracy for determining the amount of water in a sample via a Karl Fischer reaction, wherein each water determination does not require titration from one endpoint to another identical endpoint. More particularly, each water determination is made using a calibration of a sensor electrical current relative to the water equivalent of a known amount of titrant, together with the change in sensor electrical current that occurs when the sample is added to the K.F. reagent.

2. Description of the Prior Art

The determination of water content of a sample is important in many commercial products. For example, minute quantities of water in chemical process streams are detrimental for certain reactions. Further, the electrical properties of insulators are strongly dependent on water traces, and the water content of fluids such as gasoline has to be kept below a certain level. From these few examples, it is apparent that water determinations are among the most frequently performed analyses in many laboratories.

The currently most widely practiced water determination method is the "Karl Fischer" method, named after its originator who described the basis of this method in Zeitschrift Fuer Angewandte Chemie, Vol. 48, pages 394-396 (1935). In this method, the sample containing an unknown amount of water is added to a Karl Fischer reagent, hereinafter denoted K.F. reagent. This reagent is usually a solution of iodine and sulfur dioxide in pyridine and methanol or other solvents. Pyridine-free solutions are also well known in the art. The present state of the art is described in a book by E. Scholz entitled "Karl Fischer Titration", published by Springer-Verlag, N.Y. 1984. Typically, a titrant contains iodine or a mixture of iodine, $SO_2$, and amine. The vessel solution (solution) is contained in a titration vessel and typically is an alcohol or a mixture of alcohol, $SO_2$, and amine.

Present volumetric Karl Fischer titrators pretitrate to an endpoint, where an endpoint is defined as a small excess of a concentration of iodine in the vessel solution. After this, a sample is added to the titration vessel. The titration vessel is then titrated by adding an iodine-containing titrant so that the same endpoint is reached. The amount of water in the sample is determined based on the volume of Karl Fischer titrant that has been added to the sample-reagent solution in order to return to the same endpoint. To improve accuracy, these automatic titrators may correct for drift, which is usually due to water which enters the titrating vessel over time, even when no sample is added to the titration vessel. As is known in the art, drift can also be caused by many factors including the consumption of iodine by materials other than water which may be present in the titration vessel. However, the primary cause of drift generally is the water which leaks into the titration vessel from the atmosphere.

In these automatic titrators, the presence of iodine in the titration vessel is noted by a sensor. These sensors generally include two metal electrodes coupled to a sensing circuit selected from many well-known types. One commonly used circuit passes a constant current through the electrodes and measures the voltage across the electrodes. Another applies a constant voltage (d.c. or a.c.) to the electrodes and measures the current. When the amount of iodine in the solution is increased, the current level increases while, when a sample is added to the titration vessel, the amount of iodine is depleted and the current level decreases.

As noted, conventional titrators titrate from one endpoint to another identical endpoint. When the sample is present, the iodine concentration in the titration vessel decreases and the sensor current drops to a different level. After a period of a few seconds to allow the sample-reagent reaction to occur, iodine-containing titrant is added to increase the sensor current to its original level just prior to adding the sample. However, this is not always easy to accomplish, since titrant must be added very slowly as the desired current level is approached in order not to have an overshoot. The presence of any overshoot would cause error. Further, since the titrant is added very slowly toward the end of the titration step, such determinations require considerable amounts of time. In order to improve accuracy and speed in these conventional automatic titrators, two set points for the addition of titrants are frequently used. If the sensor current falls below the lower of the two set points, the titrator adds reagent at high speed. The next set point corresponds to the desired endpoint which is the current level just prior to when the sample was added to the titration vessel. Smaller amounts of titrant are added until this is reached. Other advanced titrators gradually reduce the titration speed as they approach the endpoint.

As noted, many variations of automatic titrators are found in the art, and are illustrated by the instruments described in U.S. Pat. Nos. 4,211,614 and 3,726,778. Further reference is made to the aforementioned text by E. Scholtz entitled "Karl Fischer Titration". These references generally describe various aspects of automatic titrators including endpoint drift correction.

As is apparent from the foregoing, automatic titration methods and apparatus in which titration must be from one endpoint to another identical endpoint require a considerable amount of time for each sample water determination, and are prone to errors due to overshoots in adding titrant. Each water determination requires that titrant be added and, whether or not multiple set points are used to approach the desired endpoint, a considerable amount of time is needed for each water determination. Moreover, the accuracy and sensitivity of each titration is limited by the accuracy of the mechanical components, i.e., the buret drive, of the titrator. The smallest amount of water that can be measured is determined by the precision of that buret drive. In contrast with this, the present invention does not require titration from one endpoint to another identical endpoint. In some cases it does not even require the addition of titrant in order to determine the water content of a sample, i.e., water amounts smaller than those given by the mechanical precision of the titrator can be measured. Still further, drift corrections can be made as the water determinations proceed, the method and apparatus providing improved accuracy and speed over conventionally known titrators.

Accordingly, it is a primary object of the present invention to provide titration techniques that exhibit improved speed and accuracy when used for water determination by the Karl Fischer method.

It is another object of this invention to provide improved automatic titration methods wherein water sample determinations can be made without necessarily requiring the addition of a titrant to a vessel solution containing the K.F. reagent and the sample to be analyzed.

It is another object of this invention to provide improved automatic titration methods wherein continuously updated drift corrections can be applied.

It is another object of this invention to provide improved automatic titration methods for determining water content of a sample by Karl Fischer reactions wherein the necessity of titrating from one endpoint to another identical endpoint is not required.

It is another object of this invention to provide improved automatic titration methods wherein continuous drift correction can be implemented in a very small amount of time, leading to improved accuracy of water determination.

It is another object of this invention to provide a technique that will quickly enable the validation of previously obtained results to determine water content.

BRIEF SUMMARY OF THE INVENTION

Improved K.F. water determinations for determining the amount of water in a sample are achieved in the present invention by using a calibration of the sensor output relative to the water equivalent of a known amount of titrant together with the change in sensor output that occurs when a sample is added to the titration vessel. This eliminates the need for titration from one endpoint to another identical end point. As long as iodine is present in the K.F. reagent, the strength (amount of water that reacts with a fixed amount of reagent) of the K.F. reagent can be used to determine the water content of a sample, based on the difference in the sensor output (such as the sensor current level) at the time the sample is added and the sensor output when the sample-reagent reaction is completed. The titrator apparatus can automatically keep the iodine content of the reagent in a range where this improved technique can be utilized for each sample determination. This same principle is also used to continuously correct for drift.

The apparatus broadly includes a titrator of a type known in the art, a reaction vessel in which the K.F. reagent and sample are placed together with stirring apparatus for homogenizing the vessel solution, means for introducing the iodine-containing titrant into the reaction vessel, and a sensor for determining the amount of iodine present in the reaction vessel. Typically, the means for introducing titrant is a buret loaded with the K.F. titrant and having associated therewith a buret drive. The sensor is preferably a conventional dual platinum electrode sensor. A constant voltage is applied between the two electrodes and the electrical current flowing between two electrode wires is an indication of the amount of iodine present in the vessel solution. These automatic titrators can have computing apparatus connected to them to automatically program drift corrections as well as for initiating the addition of titrant to the vessel solution at times corresponding to different current levels as noted by the sensor, and during analysis of samples, and for making the calibration computations and for computing the results.

It is often the situation that sensor electrodes become dirty during prolonged measurements. This can create a problem if it is realized too late (or not realized at all) that previous measurements are invalid. In the practice of the present invention, previous results can be quickly validated by checking the sensor calibration to insure that it remains substantially the same.

These and other objects, features, any advantages will be apparent from the following more particular description of the preferred embodiments.

BRIEF DESCRIPTION OF THE DRAWINGS

FIG. 3 illustrates drift correction in the present method.

DETAILED DESCRIPTION OF THE PREFERRED EMBODIMENTS

Apparatus

Figure 1:
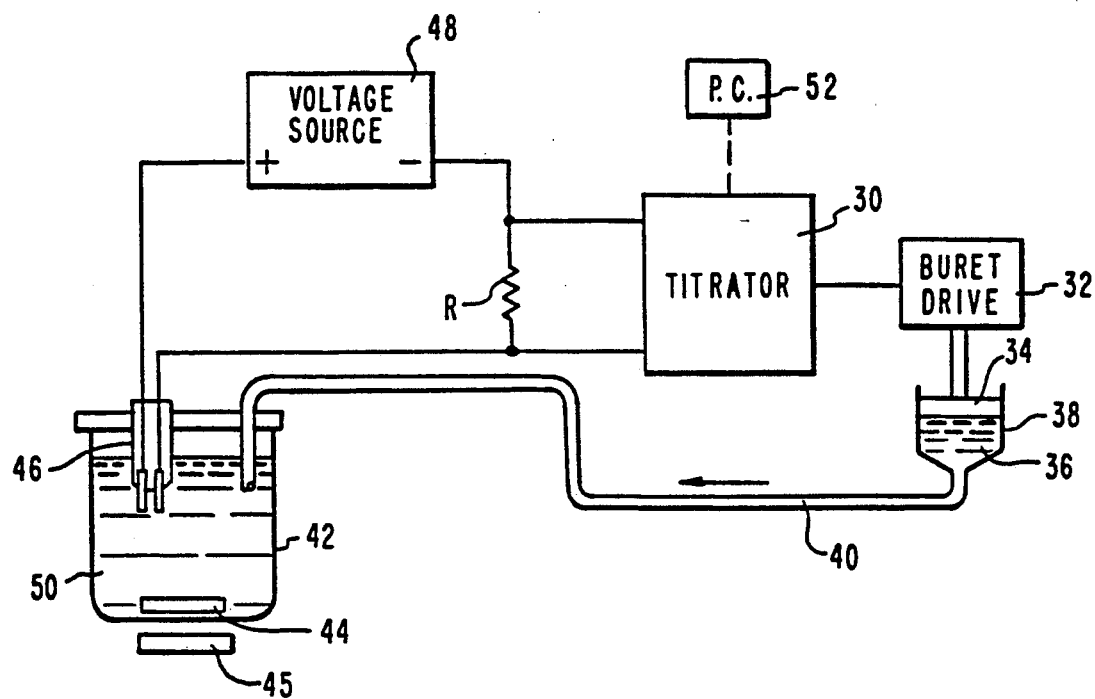
FIG. 1 schematically illustrates an apparatus for performing the improved titration techniques of this invention.

FIG. 1 schematically illustrates an apparatus suitable for the practice of the present invention. The apparatus generally comprises a titrator 30 which is of a type well known in the art. Titrator 30 is connected to a buret drive 32 which in turn operates a piston 34 for dispensing K.F. titrant 36 from buret 38. The dispensed titrant flows through tubing 40 and into the reaction vessel 42. A magnetic stirrer 44 is located in vessel 42, and is used to homogenize solutions present in the reaction vessel when activated by the magnetic stirrer drive unit 45.

A sensor electrode 46 is also located in reaction vessel 42, and is connected to an electrical source 48. The sensor is used to determine endpoints of reactions, and is preferably a dual platinum electrode sensor which is well known in the art. Such sensors generally are comprised of two platinum wires exposed to the titration vessel solution. A dc voltage of about 300 mV is applied between the sensor wires by the voltage source 48, and the electric current flowing between the two wires is measured, usually in the microampere range. This produces a voltage across the resistor R which is an input to the automatic titrator 30. Depending upon the voltage across the resistance R, and consequently the current flow in vessel 42, the automatic titrator will trigger the buret drive 32 to inject titrant into the vessel 42.

In the practice of this invention, it has been found that the current (i.e., sensor output) between the platinum wires of sensor 46 is proportional to the concentration of iodine in a Karl Fischer vessel solution 50. When a sample is added to the vessel solution the iodine content decreases and the current between the platinum sensor wires also decreases. When a larger amount of iodine is present in the vessel solution 50 because iodine containing K.F. titrant is injected into the reaction vessel, the sensor current will increase.

The titrator 30 can be connected to a computer 52 in order to trigger any operation of the titrator in response to signals from the computer. Most conventional titrators, as presently used, accomodate various operational modes to correct for factors such as drift.

IMPROVED TITRATION METHOD (FIG. 2)

As mentioned previously, the apparatus of FIG. 1 can be used for rapid titrations with improved accuracy. This can be illustrated more particularly with respect to FIG. 2, which is a plot of sensor electrode current I as a function of time. As will be seen, the operation of the automatic titrator will be illustrated with respect to the addition of three samples to the vessel solution at three separate times, each sample introducing a different amount of water into the vessel solution. Still further, analysis of water content in each of the samples is achieved without the necessity of titrating from one endpoint to an identical endpoint and, in some cases, titrants need not be introduced into the vessel solution in order to determine water content.

More specifically, the heavy dark line illustrates the sensor current over time, the various times being designated by the points 1, 2, 3, . . . 16. For each of these reference times, $T_1$, $T_2$, $T_3$, . . . $T_{16}$, a corresponding sensor electrode current $I_1$, $I_2$, $I_3$, . . . $I_{16}$ is measured and noted by the titrator 30. For example, at time $T_3$ the sensor electrode current is $I_3$.

It is noted that the sensor current level fluctuates continuously due to velocity variations in the fluid.

Many techniques are known to average out these fluctuations: for example, numerical averaging, electronic averaging, and graphic averaging. These various techniques and their application are not the object of this invention.

The titrator 30 is programmed to have two set point levels corresponding to two levels of sensor electrode current. These set point levels are designated S1 and S2 and are shown as dashed lines in FIGS. 2. The set points are operational points for the apparatus, and are used to determine when the titrator 30 shall automatically introduce titrant into the vessel solution 50. As will be appreciated more fully later, when the sensor electrode current drops so that a current corresponding to set point S1 is reached, titrator 30 will automatically introduce a fixed, known amount of titrant into the reaction vessel 42. Further, when the sensor electrode current drops below set point S2, titrator 30 automatically injects a sufficient amount of titrant into reaction vessel 42 to raise the current level above that of set point S1.

As will be seen more fully later, set points S1 and S2 are used to keep the operating region for analysis in a range of electrode current values such that water determinations can be made without the necessity of titrating from one endpoint to another identical endpoint. In the practice of this invention, a proportionality between titrant strength and the amount of water introduced by a sample is used to calculate the water content of each sample. By knowing the water equivalent of a known amount of titrant (i.e., the amount of water that reacts with a given volume of titrant) the amount of water in each sample can be determined without the necessity of titrating to an identical endpoint.

Figure 2:
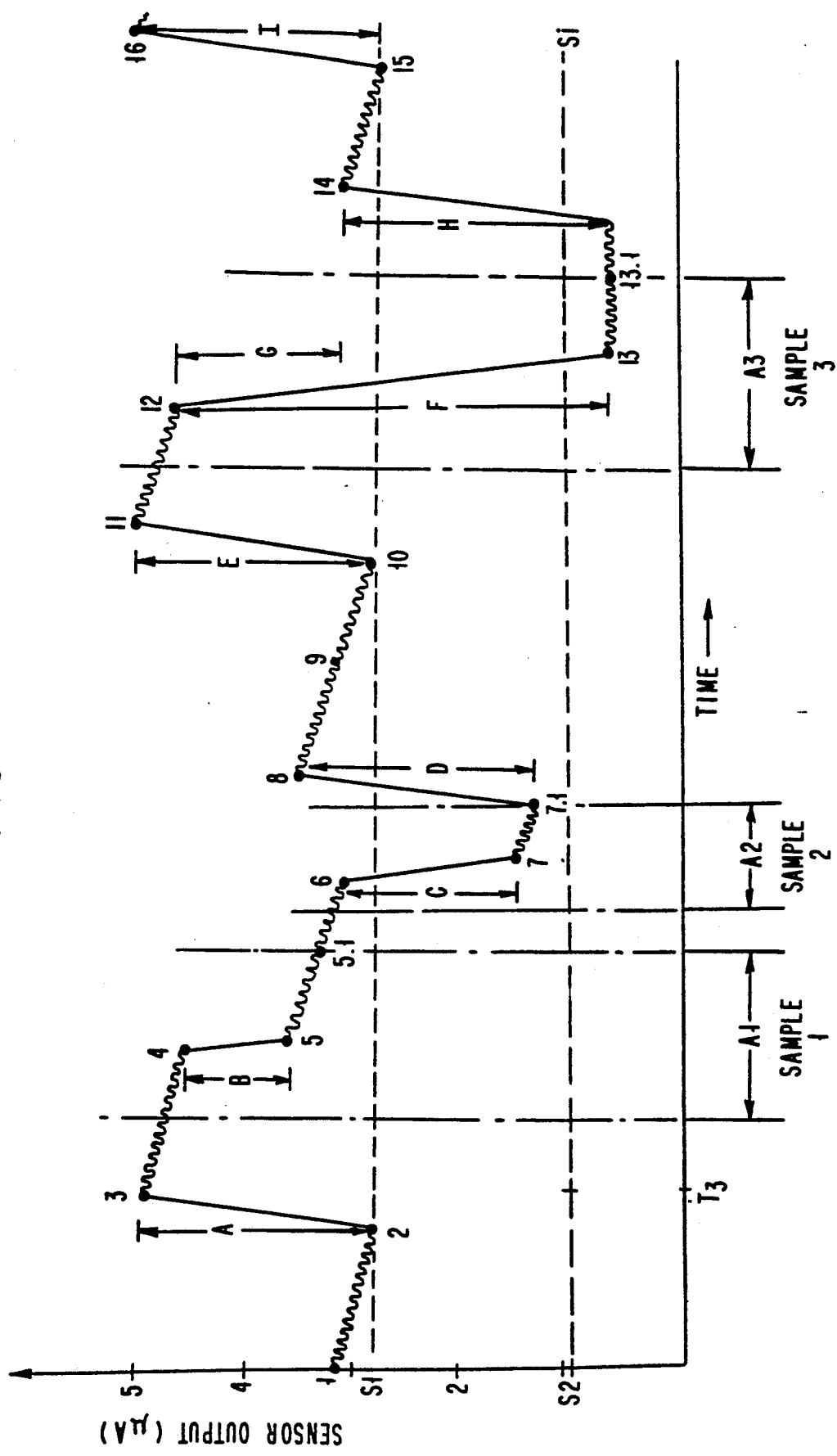
FIG. 2 is a plot of sensor electrical current versus time for a plurality of sample determinations, illustrating the improved titration method of the apparatus to effect water determination without requiring titration from one endpoint to another identical endpoint.

Referring to FIG. 2, at time $T_1$ the electrode current is $I_1$. In the passage of time, drift occurs and the electrode current decreases until at point 2, it is equal to the set point current S1. This is an operational trigger to the titrator 30, which then injects a fixed, known amount of iodine-containing titrant into the reaction vessel 42. This increases the sensor electrode current by an amount A, bringing the sensor current to a level of $I_3$ at point 3. Since the titrant was precalibrated and has a known water equivalent, this can be used for future calculations of the amount of water present in a sample. For example, the strength of the titrant may be 5 mg $H_2O$/mL, meaning that 5 mg of water reacts with 1 ml of reagent. If 5 $\mu$l of titrant were added to increase the sensor current by the amount A, then a water equivalent of 25 $\mu$g would be present.

EXAMPLE I: ADDITION OF A SAMPLE CAUSING CURRENT TO DROP A DISTANCE WHICH IS NOT BELOW SET POINT S1

At all times thus far, the apparatus has been in the standby mode. In this mode, a fixed, known amount of titrant is automatically added whenever the sensor current level decreases to set point S1. However, in the analysis mode, which is used whenever the water content of a sample is to be determined, there is no automatic injection of titrant into the vessel solution when the sensor current falls below set point S1. Also, when the apparatus is in the analysis mode, there is an automatic injection of titrant into the vessel solution whenever the sensor current level falls below the set point S2.

Between points 3 and 4 the current again decreases due to drift. At point 4, the user adds a sample to the vessel solution, causing the sensor current to drop an amount B to point 5. Titrator 30 waits a few seconds (point 5 to point 5.1) in order to calculate the amount B. The water contained in this sample is calculated as follows:

$$Water\ Content = (B/A)Y,$$

where Y is the water equivalent contained in the known, fixed amount of titrant which caused the current to rise by the amount A.

In this example, it was not necessary to add titrant to titrate back to an endpoint that is identical to the current level $I_4$ at $T_4$ (when the sample was added). Instead, the water contained in the sample is calculated directly using the water equivalent of the titrant that was added at time $T_2$.

When the titrator waits a few seconds from point 5 to point 5.1 in order to calculate the amount B, a drift correction must be made in order to subtract the amount of water introduced by drift between points 4 and 5.1. While the sample-reagent reaction is usually fast, the electrode current reading is somewhat undulating, and the titrator waits a few seconds to average out the current fluctuations. Also, the sample reagent solution is homogenized by the stirrer 44 and the titrator 30 observes the drift rate to insure that it is substantially that which was previously present. Knowing the slope of the drift rate curve, a subtraction for the amount of water introduced by drift (from point 4 to point 5.1) can be made.

In this example, if 0.1 ml of titrant of titer strength 5 mg $H_2O$/mL were added in going from point 2 to point 3, it would have a water equivalent of 0.5 mg (i.e., Y=0.5 mg. water). This water equivalent causes current to rise the fixed amount A. Different water equivalents would cause the current to rise by different amounts.

EXAMPLE II: ADDITION OF SAMPLE CAUSING SENSOR CURRENT TO FALL BELOW SET POINT S1, BUT NOT SET POINT S2

From point 5.1 to point 6, the sensor current continues to decrease due to drift. At point 6, a second sample is added causing the current level to drop an amount C (to point 7). The titrator 30 waits a few seconds (from point 7 to point 7.1) to average out the current and to allow the sample-reagent reaction to be completed and to calculate the amount C. The water content of this second sample is given by the following expression:

$$water\ content = (C/A)Y$$

where Y is the water equivalent of the known amount of titrant which caused the sensor current to rise the amount A. The current change due to the addition of this second sample is directly proportional and can be calculated by this simple ratio. Again, there is no need to add titrant to titrate to an endpoint identical to the current level at point 6 when the sample was added to the vessel solution.

As in the previous calculation with respect to the first sample, the titrator applies the appropriate drift correction in order to subtract the amount of water introduced by drift between point 7 and point 7.1.

At point 7.1, the titrator 30 injects titrant into the vessel solution so that the current level rises above set point S1. This produces an increase of current D. The titrator keeps track of the amount of titrant introduced to have the current increase by amount D. The water content of this second sample can be recalculated to verify the previously obtained amount using the following expression:

$$water\ content = (C/D)Y$$

where Y is the known water equivalent of the known amount of reagent causing the sensor current to rise the amount D. Even in this example, where titrant is added after the sample is introduced, it is not necessary that the endpoint ($I_8$) be identical to the starting point ($I_6$) at point 6 in order to provide an accurate result. This addition of titrant after the sample was introduced is generally called "post-calibration", while the introduction of titrant prior to the addition of a sample is generally called "pre-calibration".

Atmospheric drift again causes the sensor current to decrease until it reaches the current level of set point S1 at point 10. The titrator, being in a standby mode at this time, automatically injects a fixed known amount of titrant into the vessel solution. This is indicated by the current rise from point 10 to point 11, the current increasing by an amount E. The amount of titrant and its strength is identical to that introduced at point 2, so that $A = E$.

EXAMPLE III: ADDITION OF SAMPLE CAUSING SENSOR CURRENT TO DROP BELOW SET POINT S2

From point 11 to point 12, the sensor current decreases due to drift. At point 12, the user adds a third sample with a large water content, causing the sensor current to drop an amount F to point 13. Point 13 is below set point level S2, triggering an automatic response of the titrator 30 to add titrant. The sample-reagent reaction is allowed to go to completion (point 13 to point 13.1, and from 13.1 to point 14 titrant is added until the current level reaches and slightly overshoots set point S1. This raises the current level an amount H. The amount of titrant added to increase the current level to that of point 14 is recorded in the titrator 30. In this water determination, the water content of the third sample is given by the following expression:

$$water\ content = (titrant\ volume) \times (titrant\ strength) + (G/E)Y$$

where $G = F - H$. It should be noted that point 14 need not be at the same current level as the starting point 12. In conventional titrators, these different endpoints will result in an error; however, in the present invention these different endpoints are taken into account by the error correction $(G/E)Y$. This results in greater accuracy.

When the current level drops below that of set point S2, titrant is automatically added to produce a vessel solution containing iodine. Titrant is added and the volume of titrant added is noted, as in conventional titrators. However, the proportionality adjustment of the invention is used in the range where iodine is present in the solution in order to provide the correction $(G/E)Y$. Thus, even in this example it is not necessary to titrate back to an identical endpoint.

From point 14 to point 15, the titrator is in the standby mode and drift occurs. When the current level reaches point S1, titrator 3 automatically injects a fixed known amount of titrant into the reaction vessel, causing the current to increase an amount $I = E = A$. The previous result for water determination can be checked by the following expression:

$$water\ content = titrant\ volume + (G/I)Y$$

where Y is the water equivalent of the known amount of reagent which caused the current to rise by an amount I. The error which would be present in a conventional titrator is corrected for in this invention by the expression $(G/I)Y$.

SUMMARY OF EXAMPLES

It is again noted that the water determination for samples 1 and 2 was done without the necessity for titrating. All water determinations can be obtained without titrating as long as the sensor current does not fall below set point S2. This results in faster water determinations, since the user does not have to worry about slowly approaching a designated endpoint. Also, improved accuracy results since this invention does not require an identical endpoint for water determination.

The titrant additions causing sensor current rises A, D, E, and I are generally known as calibrations. For each of these titrant additions, a known amount of titrant with a water equivalent Y was added. While the volume of titrant which was added to produce current rise D need not be equal to the volume of titrant causing current rises A, E, and I, it is recognized that there may be small variations in the change of current at different times, due to changes in the solution in the titration vessel. Some of these changes include, for example, volume changes, viscosity changes, and temperature changes.

The water content of a sample to be analyzed may be based either on pre-calibration (i.e., adding the titrant before sample addition) or post-calibration (i.e., adding the titrant after the sample addition), or both (as was illustrated with respect to the second sample). Post-calibration is usually preferred, however, since it reflects changes in the solution which may have taken place due to sample addition (for example, a volume change). The titrator 30 can store and compare subsequent calibrations for added reliability of the results.

A further improvement on the calibration procedure which takes into account the possibility of titrant leakage is as follows: when no samples are being run, a small amount of titrant may leak out of the tubing tip that is immersed in the titration vessel solution. The amount of titrant leaking out increases with time. If the next calibration procedure is performed after a considerable time has passed, the amount of titrant dispensed may be smaller because of this effect. To overcome this error, the titrator 30 first dispenses a small amount (for example, 10 microliters), and does not use this data for calibration. Then, after a short time (for example, 10 seconds) the actual titrant dispensing used for calibration is performed. This procedure is only necessary in the case where the samples are not run for awhile. When the titrator is actually used for analysis, the dispensing steps are performed so frequently that no such procedure is necessary. As an alternative, error can be avoided by making the amount of titrant dispensed sufficiently large that the leaked-out volume is negligible.

SET POINTS S1 AND S2

These operating set points can be chosen with wide latitude, and are typically set so that the sample analysis is primarily within the range where iodine is present in the vessel solution so that the proportionality between sensor current change and titrant water equivalent can be used for water determinations. As long as no sample is being run (standby mode) the titrator will keep the sensor current above set point S1 by adding the same, known amount of titrant each time the current level decreases to that of set point level S1. However, in the analysis mode wherein samples are to be analyzed (during the timebands A1, A2, A3) no titrant is added when the current level drops below set point level S1. This is because the addition of titrant at this time would cause error. During the analysis mode, which can be initiated by having the user press a button and automatically concluded by the titrator, no titrant is added when the current drops below set point level S1. If the sensor current level is above S1 after the analysis mode is complete, no titrant is added. If the sensor current level is between S1 and S2 after the analysis mode is complete, the titrator calibrates back to a current level above set point S1. This provides a greater range over which the invention can be used and accomodates samples having larger water contents. If the current level is below S2 after the analysis mode, titrant is added until the current level exceeds set point S1.

Generally, the lower set point level S2 is chosen to be that close to where the proportionality between sensor current value and iodine content disappears. Typically, this is at very low current levels where the vessel solution is generally considered "wet", i.e., essentially devoid of iodine. The spread between set point levels S1 and S2 is chosen not to be too narrow so that titrants won't be too quickly added if the sample causes the current level to drop below S1. On the other hand, the separation between S1 and S2 is chosen to be not so wide that the sensor current will loose its proportionality to the iodine concentration. That is, it is desirable that the sensor current be proportional to iodine concentration over the entire range between S1 and S2.

The use of two set point levels to slowly approach the desired end point of a reaction has already been noted. Previously mentioned patents U.S. Pat. No. 4,211,614 and U.S. Pat. No. 3,726,778 describe the use of "bands" where the bands are the current levels between two titrator set points, in order to keep the titrator in a close operational mode. However, this is different than the use of the two set points in the present application, where this aspect (two set points) is only used to provide triggering points so that titrant can be added to the reaction vessel in order to be in the range where the proportionalities described hereinabove are used to determine the water content of the sample. By establishing a scale consisting of a specific water equivalent of reagent which causes a specific rise in sensor electrical current, the water content of a sample can be computed simply by using the drop in sensor electrode current. The scale used for this proportionality can be made either before sample addition (precalibration) or after sample addition (postcalibration).

Drift Correction

As in all automatic titration apparatus, drift effects have to be corrected. Techniques for this are known in the art, and can be seen by referring to U.S. Pat. No. 4,211,614. These techniques can be directly programmed into the titrator control apparatus to provide the necessary correction.

In practice, the drift of a vessel solution can be determined ahead of time and programmed into the titrator or, as in the present invention, can be determined at any time. Thus, the present invention keeps track of the sensor current levels and the time periods over which drift occurs. Knowing these, the slope of the sensor electrode current during drift can be calculated at any time. Knowing the slope, the sensor current offset due to drift can be applied to each sample water determination (without the need to add titrant to compensate for drift). Generally, all sensor currents have to be averaged over at least several seconds and the drift corrected.

Drift is a factor which limits the accuracy of a Karl Fischer titration. Drift is defined as the change of the endpoint which is caused by the introduction of water traces due to imperfect seals of the titration vessel and by chemical side reactions which consume iodine in the titration vessel. It is apparent that such drift has to be deducted from the result to arrive at the actual "net" water the sample actually contained.

FIG. 3 shows a record of sensor current over time. The current change during equal periods of time, say 10 seconds, is marked as P, Q, and R, respectively. It should be noted that after proper calibration, as noted previously, P, Q, and R also represent micrograms of water directly (i.e., a water equivalent). A sample is introduced at time $T_1$, causing the sensor output to decrease rapidly.

In operation, the result of the analysis, Q, has to be corrected for drift.

Drift correction can be accomplished in two ways: (1) the drift can be measured before analysis. In this case the result is

*correct water amount* $= Q - P$ (2) the drift can be measured after analysis. In this case, the result is

*correct water amount* = Q − R

There are advantages and disadvantages for both methods.

Method (1) has the advantage that the result is available at time $T_2$, i.e., immediately after completion of the analysis. Method (2) has the disadvantage that the result is available later at time $T_3$. The advantage of method (2), however, is that the new drift, R, reflects the actual composition of the analysis mixture after therefore sample addition. Therefore, method (two) is responsive if a new drift were caused by additional side reactions.

If the sample contains components which contribute to drift (i.e., cause side reactions), the second method is more accurate and desirable. However, if it is known that the sample components will not contribute in a significant way to drift, then the first method is desireable, since drift correction can be done very quickly. Whatever method is used, there is no need to add titrant.

Both methods are superior to drift corrections as carried out by present conventional titrators. Conventional titrators have to actually titrate, i.e., add titrant, to the mixture. In order to arrive at a reasonable drift rate these titrant additions have to be averaged over at least one minute or more. In the practice of this invention drift corrections can be done in "real time" in a much shorter time.

The repeated measurements of the increase of sensor current due to titration additions (calibrations) may serve to monitor the cleanliness of the sensor electrodes as well as the rest of the apparatus. For example, a common problem in KF analysis is the coating of the sensor electrodes by oils, which affects the sensor current output. Referring to FIG. 2, calibration responses A, D, E and I (expressed in sensor response per volume unit of titrant addition) are substantially equal as long as the sensor electrodes are clean and the system is functioning properly. If the calibrations are quite unequal, the operator is immediately aware that there is a malfunction in the system. As an example, if the calibrations vary by in excess of about 10%, the system components must be checked and the results must be considered unreliable.

Volume corrections may also be applied to the titrator 30. For example, if the initial volume in the titration vessel is 100 mL and the sample volume is 5 mL, the sensor electrode current will drop by 5%, even if no water is present. This correction is easily applied by entering the sample volume into the titrator, which automatically will correct for a small drop in electrode current due to volume change.

Additional Apparatus

It will also be apparent to those of skill in the art that the present invention is applicable to coulometric titrators. In such titrators, the electrode current is measured by passing a known amount of electric charge through the titrator instead of adding a known volume of titrant volumetrically. Whether sensor voltage or sensor current is indicative of the iodine present in the system the invention can be used to provide rapid and accurate water determinations.

Instead of frequently establishing the relationship between sensor electrode current and a water equivalent, it is also possible to use a fixed relationship which may be programmed into the titrator and used to determine water content. Again, there is no need to titrate to an identical endpoint.

While it has been found preferrable to use a dual platinum electrode sensor, other sensors can be used. The sensor electrodes may be of different lengths and may be formed into loops instead of straight wires, etc. Electrodes where the two wires are made of different materials can also be used.

In laboratory work, a constant voltage between the two electrodes of about 300 mV d.c. has been used. In general, the constant dc voltage should be no less than about 100 mV and no more than about 600 mV. The electrode reaction at the negative electrode is $I_2 + 2e = 2 I^-$, while the electrode reaction at the positive electrode is $2I^- - 2e = I_2$. The electrodes sense the presence of $I_2$ in the solution, i.e., the more $I_2$ the higher the current ($I^-$ is always at an excess). However, electrodes driven by an ac current source have also been used in the art and can be applied in the practice of the present invention.

The invention has been described as using a titrant with a known titer strength. In actual practice, however, the titer strength is first determined by titrating a known amount of water and using the test result to determine the strength of the solution. This strength is then used in all the procedures described hereinabove.

As was noted previously, water determinations of the first two samples (FIG. 2) always fell within the range in which the proportionality between current drop and titrant water equivalent could be used. In practice, it has been found that this proportionality (calibration) can also be extrapolated to points outside the actual calibration range, i.e., to current levels somewhat less than the current levels of set point S2. Thus, the calibration curve (current per titrant addition) has been found to be valid over ranges which exceed the actual calibration ranges.

Experimental Results

Considerable laboratory demonstrations of the present invention have illustrated the improved speed and accuracy that results. In one such series of laboratory activity to verify the water content of samples having known water contents, a recorder was connected to the reaction vessel and a dual platinum electrode sensor was used to provide current inputs to the recorder. A dc voltage of 300 mV was applied to the dual platinum electrodes and the water-containing samples and titrant were manually added to the reaction vessel from syringes. A magnetic stirrer having a constant speed was used to homogenize the Karl Fischer vessel solution. In this procedure, the titration vessel solution was 200 mL ERICSEN vessel solution Cat No. 16-03-1A produced and sold by Ericsen Instruments, Inc. This vessel solution was a solution of sulfur dioxide and amine, in a mixture of methanol and chloroform. The titrant was a solution of iodine in xylene having a water equivalent 0.181 mg $H_2O$/mL, which was added to the vessel by a buret.

The technique of the present invention was carried out and the recorder graphically displayed the changes in sensor current due to the addition of samples and titrant. Electrode current levels were graphically averaged and the drift was corrected, the recorder plot showing excellent accuracy to better than ±1 microgram of water. This is an accuracy which is not achievable using presently known volumetric titrators.

What has been described is an improved technique for performing automatic titrations in which the necessity of titrating to an endpoint identical to that of the starting point is not required. This technique provides faster titration results and improved accuracy since the invention calculates the required parameters based only on the strength of the titrant reagent and on the relative values of the beginning and endpoint of sensor current when a sample is added and when the sample-reagent reaction is complete. Thus, in the practice of this invention a proportionality, or calibration, is determined by first measuring the sensor output (electrode current) then adding a known amount of reagent having a known water equivalent, measuring the sensor output (electrode current) after this addition of reagent, and using the difference between the first and second sensor outputs (electrode currents) to determine a calibration quantity. In this manner, a water equivalent for that amount of reagent is determined. A sample to be analyzed is added to the reagent and the calibration (or proportionality) is used to calculate the water content of the sample. To do so, the sensor electrode current is measured just prior to adding the sample, after which the unknown sample is added and the new sensor electrode current is measured. The water content of the sample is determined by calculating the difference of the first and second sensor electrode currents and multiplying that difference by the calibration, or proportionality, in order to determine the water content of the sample.

While the invention has been described with respect to particular embodiments thereof, it will be apparent to those of skill in the art that variations can be made therein without departing from the spirit and scope of the present invention. For example, the apparatus used to provide automatic titration in accordance with the present invention can be varied, as can the vessel solutions and titrants that are employed. The general concept of calibrating the sensor with a known amount of titrant prior to (or after) the actual titration is particularly unique to water determinations by the Karl Fischer Method.

Having thus described my invention what I claim as new and desire to secure as Letters Patent, is:

1. A method to determine the water content of a sample by the Karl Fischer method, including the steps of:
    providing a solution having a sensor immersed therein which provides an output indicative of the iodine content of said solution,
    adding a known amount of iodine to said solution,
    measuring a first change in output of said sensor due to the addition of said iodine to establish a calibration for said sensor, said calibration relating the change in sensor output to an equivalent water amount,
    adding a sample to said solution, said sample having a water content to be determined,
    measuring a second change in sensor output due to the addition of said sample, and
    using said second change in sensor output and said calibration to determine the water content of said sample.

2. The method of claim 1, wherein said calibration is established prior to the addition of said sample to said solution.

3. The method of claim 1, wherein said calibration is established subsequent to the addition of said sample to said solution.

4. The method of claim 1, wherein said sensor output is an electrical current through said sensor.

5. The method of claim 4, wherein said sensor is a multi-electrode sensor, there being a constant voltage applied across said electrodes.

6. The method of claim 1, including the further step of correcting for drift that occurs during the analysis of sample water content by using said calibration and subtracting said drift from said second change.

7. The method of claim 1, including the further step of adding iodine to said vessel solution after said sample is added and using the amount of iodine added together with said calibration to determine the water content of said sample.

8. The method of claim 1, wherein the water content of a plurality of samples is measured using said calibration and the change in sensor output which occurs when each of said samples is added to said solution.

9. The method of claim 1, wherein said iodine is in a known amount of titrant added to said solution.

10. The method of claim 1, wherein said solution is capable of electrically generating iodine, and said known amount of iodine is added to said solution by passing a known amount of electric charge through said solution.

11. The method of claim 1, wherein said solution is stirred during said measuring steps.

12. A method for determining the water content of a sample by the Karl Fischer reaction, including the steps of:
    adding a known amount of iodine to a solution and wherein a sensor is located in said solution, the electrical output of said sensor being proportional to the amount of iodine present in said solution,
    measuring the change in electrical output of said sensor when said iodine is added to establish a calibration relating said sensor output change to an equivalent amount of water,
    adding a sample whose water content is to be determined to said solution,
    measuring the change in electrical output of said sensor when said sample is added, and
    determining the water content of said sample by using said calibration and the change of sensor electrical output when said sample is added to said solution.

13. The method of claim 12, wherein said calibration is used to determine the water content of a plurality of samples added to said solution.

14. The method of claim 12, wherein said calibration is updated after a plurality of samples are measured for water content.

15. The method of claim 12, including the further steps of
    using said calibration to determine the water content of at least one sample,
    adding a known amount of additional iodine to said solution,
    measuring the change in electrical output of said sensor when said additional iodine is added to establish a second calibration relating the change in sensor electrical output to an equivalent amount of water,
    adding another sample to said solution, measuring the change in sensor electrical output when said another sample is added to said solution, and determining the water content of said another sample by using said change in sensor electrical output and said second calibration.

16. The method of claim 12, wherein said calibration linearly relates the change in sensor electrical output to an equivalent water amount.

17. The method of claim 12, wherein said sensor electrical output is the electrical current flowing through said sensor when a substantially constant voltage is applied across said sensor.

18. The method of claim 17, wherein the magnitude of said electrical current is proportional to the concentration of iodine in said solution.

19. The method of claim 17, wherein said sensor is a dual electrode sensor.

20. The method of claim 12, wherein said calibration is determined at least twice, said calibrations being compared to determine the accuracy of a previous calibration, and thereby the accuracy of water determinations made using said previous calibration.

21. The method of claim 12, wherein said iodine is in a known amount of titrant added to said solution.

22. The method of claim 12, wherein said solution is capable of electrically generating iodine, and said known amount of iodine is added to said solution by passing a known amount of electric charge through said solution.

23. The method of claim 12, wherein said solution is stirred during said measuring steps.

24. A method for determining the accuracy of water content measurements obtained by the Karl Fischer reaction, including the following steps:

adding a known amount of iodine to a solution, measuring the change in electrical output of a sensor located in said solution when said iodine is added to said solution to establish a first calibration relating said change in sensor electrical output to an equivalent amount of water, adding a known amount of additional iodine to said solution and measuring the change in sensor electrical output to establish a second calibration relating the change in sensor electrical output to an equivalent amount of water, and comparing said first and second calibrations to verify the water content measurement made by using said first calibration.

25. The method of claim 24, wherein said sensor is a multi-electrode sensor, there being a substantially constant voltage applied across said sensor, the output of said sensor being the electrical current flowing between said electrodes.

26. The method of claim 24, wherein said sensor is a multi-electrode sensor, there being a substantially constant current through said sensor, the output of said sensor being a change in voltage indicated by said sensor.

27. The method of claim 24, wherein said iodine is in a known amount of titrant added to said solution.

28. The method of claim 24, wherein said solution is capable of electrically generating iodine, and said known amount of iodine is added to said solution by passing a known amount of electric charge through said solution.

29. The method of claim 24, wherein said solution is stirred during said measuring step.

30. A method for determining the water content of a sample by a Karl Fischer reaction, including the steps of:

providing a solution having a sensor therein which provides an output indicative of the iodine content of said solution, adding a sample to said solution, said sample having a water content to be determined, measuring the change in sensor output due to the addition of said sample to said solution, adding a known amount of iodine to said solution, measuring the change in sensor output due to the addition of said iodine to said solution to establish a calibration for said sensor relating the change in sensor output to a water equivalent, and using said calibration and said change in sensor output due to the addition of said sample to determine the water content of said sample.

31. The method of claim 30, wherein said sensor is a multi-electrode sensor having a substantially constant voltage thereacross, current through said sensor being the output of said sensor.

32. The method of claim 31, wherein the current through said sensor is proportional to the iodine concentration of said solution.

33. The method of claim 30, including the further steps of:

adding a second sample to said solution, measuring the change in sensor output due to the addition of said second sample, and determining the water content of said second sample by using said change in sensor output when said second sample is added and said calibration.

34. The method of claim 30, including the further step of correcting for drift by using said calibration and subtracting said drift from said change in sensor output due to the addition of said sample.

35. The method of claim 30, wherein said calibration linearly relates the change in sensor output to an equivalent water amount.

36. The method of claim 30, wherein said iodine is in a known amount of titrant added to said solution.

37. The method of claim 30, wherein said solution is capable of electrically generating iodine, and said known amount of iodine is added to said solution by passing a known amount of electric charge through said solution.

38. A method for determining the water content of a sample by the Karl Fischer reaction, including the steps of:

adding iodine to a solution to establish a first non-zero level of iodine therein, there being a sensor located in said solution, the electrical output of said sensor being proportional to the amount of iodine present in said solution, adding a known amount of iodine to said solution to attain a second level of iodine therein greater than said first level, measuring the change in electrical output of said sensor when said known amount of iodine is added to establish a calibration relating said sensor output change to an equivalent amount of water, adding a sample whose water content is to be determined to said solution, measuring the change in electrical output of said sensor when said sample is added, and determining the water content of said sample by using said calibration and the change of sensor electrical output when said sample is added to said solution.

39. The method of claim 38, wherein said calibration substantially linearly relates the change in sensor electrical output to an equivalent amount of water.

40. The method of claim 38, wherein said sensor is a multielectrode sensor.

41. The method of claim 38, wherein said iodine is in a known amount of titrant added to said solution.

42. The method of claim 38, wherein said solution is capable of electrically generating iodine, and said known amount of iodine is added to said solution by passing a known amount of electric charge through said solution.

43. The method of claim 24, wherein said solution is stirred during said measuring steps.

44. A method to determine the water content of a sample by the Karl Fischer method, including the steps of:
providing a solution having a sensor therein which provides an output indicative of the iodine content of said solution,
adding a known amount of iodine to said solution, measuring a first change in output of said sensor due to the addition of said titrant to establish a calibration for said sensor, said calibration relating the change in sensor output to an equivalent water amount,
adding a sample to said solution, said sample having a water content to be determined,
measuring a second change in sensor output due to the addition of said sample,
using said second change in sensor output and said calibration to determine the water content of said sample,
measuring a third change in sensor output with time during which no sample water is added, and
using said third change in sensor output with time to correct the result for water content of said sample.

45. The method of claim 44, wherein said solution is stirred during said measuring steps.

46. A method for providing a calibration relating the electrical output of a sensor immersed in a Karl Fischer solution to an equivalent water amount comprising the following steps:
establishing an iodine level in a Karl Fischer solution as measured by a first electrical output of said sensor,
adding a known amount of water to said solution thereby changing the electrical output of said sensor to a second electrical output, and
equating the change in sensor electrical output between said first electrical output and said second electrical output to said known amount of water to establish a calibration relating sensor electrical output to a water equivalent.

47. A method for measuring drift in a Karl Fischer solution by an electrical sensor immersed therein, including the steps of
providing a Karl Fischer solution having an electrical sensor therein whose electrical output bears a substantial proportionality to the iodine concentration of said solution over a range of iodine concentration,
establishing an iodine concentration in said solution,
measuring the change in iodine concentration in said solution over a period of time by measuring the change in sensor electrical output over said period of time, and
using said change in sensor electrical output and said proportionality to establish a drift measurement during said period of time.

48. The method of claim 47, in which iodine and water are not intentionally added to said solution during said period of time.

49. The method of claim 47, including the further steps of applying said drift measurement to the analysis of a sample to determine water content.

* * * * *